US012678471B2

(12) United States Patent
Hwang et al.

(10) Patent No.: US 12,678,471 B2
(45) Date of Patent: Jul. 14, 2026

(54) METHOD FOR INHIBITING INFECTION OF SARS-CoV-2 IN A SUBJECT

(71) Applicant: Chang Gung University of Science and Technology, Taoyuan City (TW)

(72) Inventors: Tsong-Long Hwang, Taoyuan City (TW); Yu-Li Chen, Taoyuan City (TW); Michal Korinek, Kaohsiung City (TW); Marcela Safratova, Hradec kralove (CZ); Anna Hostalkova, Hradec Kralove (CZ)

(73) Assignee: Chang Gung University of Science and Technology, Taoyaun City (TW)

( * ) Notice: Subject to any disclaimer, the term of this patent is extended or adjusted under 35 U.S.C. 154(b) by 479 days.

(21) Appl. No.: 18/154,879

(22) Filed: Jan. 16, 2023

(65) Prior Publication Data

US 2023/0390351 A1     Dec. 7, 2023

(30) Foreign Application Priority Data

Jun. 1, 2022     (TW) .................................. 111120506

(51) Int. Cl.
*A61K 36/29*          (2006.01)
*A61K 31/4741*        (2006.01)
*A61P 31/14*          (2006.01)

(52) U.S. Cl.
CPC .......... *A61K 36/29* (2013.01); *A61K 31/4741* (2013.01); *A61P 31/14* (2018.01)

(58) Field of Classification Search
CPC ...... A61K 31/4741; A61K 36/29; A61P 31/14
See application file for complete search history.

(56) References Cited

U.S. PATENT DOCUMENTS

2023/0233483 A1* 7/2023 Beghyn ................... A61P 31/14
514/736

FOREIGN PATENT DOCUMENTS

EP          3906923 A1 * 11/2021 ......... A61K 31/4375
WO     WO-2021043234 A1 *  3/2021 ........... A61K 31/353

OTHER PUBLICATIONS

Joshi et al.; "Identification of Berbamine, Oxyacanthine and Rutin from Berberis asiatica as anti-SARS-CoV-2 compounds: An in silico study"; Journal of Molecular Graphics and Modelling 109 (2021); available online Oct. 11, 2021.*
Machine Translation for Roth (EP 3 906 923 A1); published Nov. 10, 2021.*
Vignesh et al.; TJPS 2022; 46(2); pp. 137-148; published Mar. 23, 2022.*
PubChem Entry for Obamegine (CID 441064); downloaded Aug. 12, 2025.*
Koutova et al.; Molecules 25; p. 964 (15 pages); published Feb. 20, 2020.*
Banete et al.; "Pathogenesis and transmission of SARS-CoV-2 D614G, Alpha, Gamma, Delta, and Omicron variants in golden hamsters"; NPJ | Viruses (3), Article 15; published: Feb. 24, 2025.*
Puttaswamy H, Gowtham HG, Ojha MD, Yadav A, Choudhir G, Raguraman V, Kongkham B, Selvaraju K, Shareef S, Gehlot P, Ahamed F, Chauhan L. In silico studies evidenced the role of structurally diverse plant secondary metabolites in reducing SARS-CoV-2 pathogenesis. Sci Rep. Nov. 25, 2020;10(1):20584. doi: 10.1038/s41598-020-77602-0.
Zhang ZR, Zhang YN, Zhang HQ, Zhang QY, Li N, Li Q, Deng CL, Zhang B, Li XD, Ye HQ. Berbamine hydrochloride potently inhibits SARS-CoV-2 infection by blocking S protein-mediated membrane fusion. PLoS Negl Trop Dis. Apr. 25, 2022;16(4):e0010363. doi: 10.1371/journal.pntd.0010363.
Leng L, Xu Z, Hong B, Zhao B, Tian Y, Wang C, Yang L, Zou Z, Li L, Liu K, Peng W, Liu J, An Z, Wang Y, Duan B, Hu Z, Zheng C, Zhang S, Li X, Li M, Liu Z, Bi Z, He T, Liu B, Fan H, Song C, Tong Y, Chen S. Cepharanthine analogs mining and genomes of Stephania accelerate anti-coronavirus drug discovery. Nat Commun. Feb. 20, 2024;15(1):1537. doi: 10.1038/s41467-024-45690-5.

* cited by examiner

*Primary Examiner* — Jeffrey T. Palenik
(74) *Attorney, Agent, or Firm* — Hannah Tien

(57)          ABSTRACT

A method for inhibiting infection of SARS-CoV-2 in a subject is provided, including administering to the subject a compound, wherein the compound comprises Aromoline, Obamegine, Berbamine or Bersavine.

7 Claims, 3 Drawing Sheets

METHOD FOR INHIBITING INFECTION OF SARS-CoV-2 IN A SUBJECT

FIELD OF THE INVENTION

The present invention relates to a method for inhibiting infection of severe acute respiratory syndrome coronavirus (SARS-CoV-2) in a subject, particularly a method for administering compounds extracted from the Berberidaceae for inhibiting infection of SARS-CoV-2 in a subject.

BACKGROUND OF THE INVENTION

Severe acute respiratory syndrome coronavirus 2 (SARS-CoV-2) is a novel member of coronavirus discovered in 2019 and belongs to the genus Betacoronavirus in the family Coronaviridae. This virus is an enveloped positive-strand single-stranded RNA virus having a genome size of about 29.7 kb, and it is the seventh known coronavirus that can infect humans. The main route of transmission of this virus is the respiratory tract, and it enters a host cell through binding of spike protein on the viral particle membrane and angiotensin-converting enzyme 2 (ACE2) on the host cell, and can infect human organs including lungs, hearts, kidneys, etc., where ACE2s are widely distributed.

SARS-CoV-2 is highly transmissible. When it enters a respiratory tract and infects lung tissues, an inflammatory response is induced, which causes damages to lung tissues and forms severe special infectious pneumonia (COVID-19), and eventually progresses to acute respiratory distress syndrome having high fatality rate. COVID-19 is a disease that has become a global pandemic, new drugs against COVID-19 are being actively developed around the world, and the important strategy of developing anti-SARS-CoV-2 drugs is to block the binding of spike proteins and ACE2.

Natural compounds have the advantages of being rich in sources and diversified skeletons, and are important bases for drug development. From 1981 to 2019, nearly half of the drugs newly approved by the U.S. Food and Drug Administration (FDA) were derived from natural products or their derivatives, for example, cocaine-derived narcotics and morphine-derived pain relievers, vincristine, doxorubicin, and paclitaxel are used for the treatment of cancers, and penicillin derived from fungi is used as an antibiotic. Accordingly, the present invention actively studies natural compounds that have the potential to be developed into new drugs against COVID-19.

DETAILED DESCRIPTION OF THE INVENTION

The present invention is a method for inhibiting infection of SARS-CoV-2 in a subject, comprising administering a compound to the subject, wherein the compound comprises Aromoline, Obamgine, Berbamine or Bersavine.

In the present invention, the compound is extracted from a plant of the barberry family (Berberidaceae).

Preferably, the compound is an alcohol (such as ethanol) extract extracted from the barberry family (Beriberidaceae).

More preferably, the plant of the barberry family (Beriberidaceae) is *Berberis vulgaris.*

After research, the present invention discovers that alkaloid compounds of *Berberis vulgaris* have the ability to inhibit viral infection.

In a more preferred embodiment, the compound of the present invention inhibits infection of SARS-CoV-2 in the subject by blocking the binding of spike protein on the SARS-CoV-2 and the angiotensin-converting enzyme 2 on the subject's cell.

The SARS-CoV-2 in the present invention is D614G variant, Delta variant or Omicron variant, more preferably, the SARS-CoV-2 in the present invention is the Delta variant or Omicron variant, and most preferably, the SARS-Cov-2 in the present invention refers is Omicron variant.

In the present invention, the subject referred in the present invention is human or mammal.

EMBODIMENTS

Figure 1:
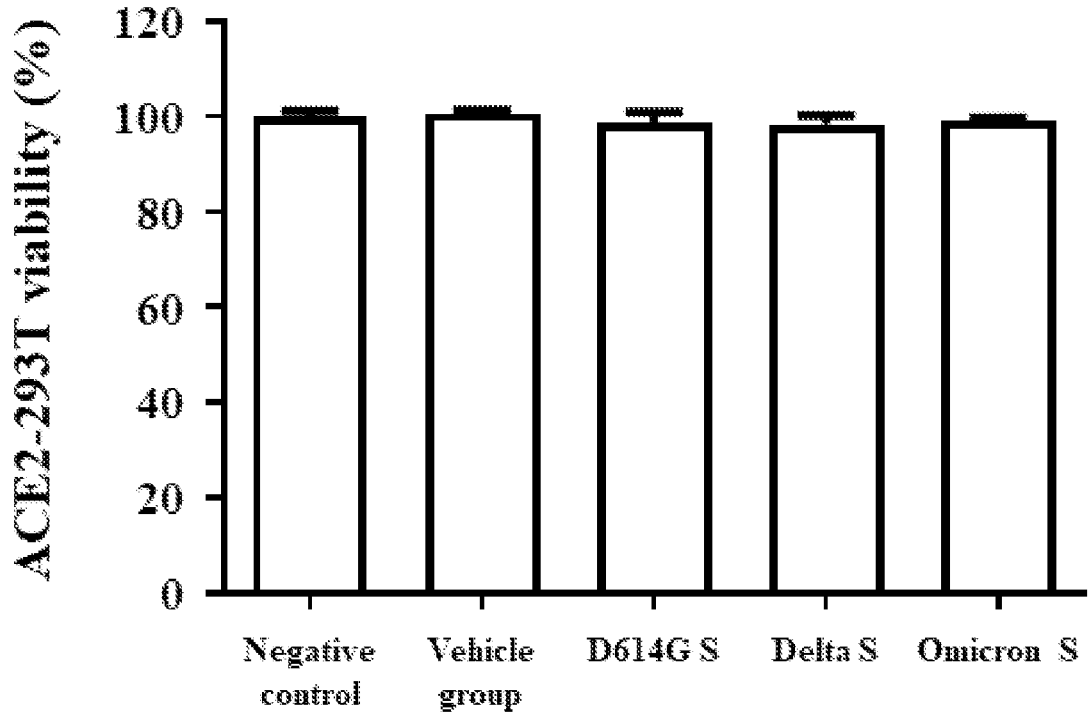
FIG. 1 shows the effect of pseudotyped lentivirus on the survival rate of ACE2-293T cells.

The detailed description of the embodiments is intended to illustrate the preferred embodiments of the present invention and is not intended to limit the present invention to certain embodiments. It should be noted that this invention is intended to cover all alternative embodiments that fall within the same spirit and scope of this invention. Some non-essential modifications and adjustments made by others according to the concept of the present invention still belong to the protection scope of the present invention.

Natural Compounds

The SARS-CoV-2 pseudotyped lentivirus screening platform was used in the present invention to screen antiviral activities. The present invention found that the alkaloid compounds contained in the plants of *Berberis vulgaris* had the ability to inhibit viral infections.

95% alcohol extract of *Berberis vulgaris* was used in the present invention, after being purified, separated and structurally identified the alkaloid compounds including Aromoline, Obamegine, Berbamine and Bersavine were evaluated for their antiviral biological activities.

Pseudotyped Lentivirus

The VSV-G pseudotyped lentivirus (clone name: S3w.Fluc.Ppuro) of the control group and the VSV-G pseudotyped lentivirus that expressed the spike protein of SARS-CoV-2 (clone name: nCoV-S-Luc-D614G; nCoV-S-Luc-B.1.617.2 and nCoV-S-Luc-B.1.1.529) used in the present invention were purchased from the RNAi Core of the Academia *Sinica*. Among them, the nCoV-S-Luc-D614G pseudotyped lentivirus expressed the spike protein of the SARS-CoV-2 D614G variant (hereinafter referred to as the D614G S protein), and the nCoV-S-Luc-B.1.617.2 pseudotyped lentivirus expressed the spike protein of the SARS-CoV-2 Delta variant (hereinafter referred to as Delta S protein), and nCoV-S-Luc-B.1.1.529 pseudotyped lentivirus expressed the spike protein of SARS-CoV-2 Omicron variant (hereinafter referred to as Omicron S protein).

Pseudotyped Lentivirus Infection Test

First, HEK-293T cells that overexpressed hACE-2 protein (hereinafter referred to as ACE2-293T cells) were seeded in a 96-well cell culture plate at 1×104 cells per well, and cultivated in an incubator at the condition of 37° C. and 5% $CO_2$.

The ACE2-293T cells were divided into a negative control group (untreated), a vehicle group (DMEM was administered), a D614G S protein group (0.5 R.I.U. of D614G S protein pseudotyped lentivirus was administered), a Delta S protein group (0.5 R.I.U. of Delta S protein pseudotyped lentivirus was administered) and an Omicron S protein group (0.5 R.I.U. of Omicron S protein pseudotyped lentivirus was administered).

0.5 relative infectious unit (R.I.U.) of Pseudotyped lentivirus per cell (0.5 R.I.U./cell; ie 5×103 R.I.U./well) were pretreated with different concentrations of antiviral agents, in a DMEM medium containing 10% of fetal bovine serum (FBS), at 37° C., for 1 hour. Then the media of the ACE2-293T cells of the D614G S protein group, the Delta S protein group, and the Omicron S protein group were replaced with the pretreated pseudotyped lentivirus solution, and cultivated for 24 hours. The vehicle group (DMEM was administered) was treated with PBS instead of the viral solution in the same treatment steps.

The infectivity of the VSVG, D614G S, Delta S and Omicron S pseudotyped lentiviral solutions were 2,682 R.I.U./μL, 737 R.I.U./μL, 190 R.I.U./μL and 1,070 R.I.U./μL, respectively. After host cells were infected, the luciferase activity was measured with a Luciferase assay system (E2520, Promega) and recorded by a fluorometer. Briefly, the ACE2-293T cells were assayed for luciferase activity by using a luciferase substrate on cell lysates according to the manufacturer's instructions.

Pseudotyped Lentivirus Cytotoxicity Analysis

After being treated for 24 hours, the ACE2-293T cells of the negative control group (untreated), the vehicle group (DMEM was administered), D614G S protein group (0.5 R.I.U. of D614G S protein pseudotyped lentivirus was administered), Delta S protein group (0.5 R.I.U. of Delta S protein pseudotyped lentivirus was administered) and Omicron S protein group (0.5 R.I.U. Omicron S protein pseudotyped lentivirus was administered) were tested for cell survival rate. The results are shown in Table 1 and FIG. 1, there were no significant differences in cell survival rates between each group.

TABLE 1

| Group Name | Cell viability (%) |
|---|---|
| Negative control group | 100.00 ± 3.37 |
| Vehicle group | 99.05 ± 3.32 |
| D614 G S | 100.83 ± 4.41 |
| Delta S | 103.06 ± 1.49 |
| Omicron S | 98.00 ± 0.91 |

Data are represented as mean value ± standard deviation (n = 3)

Compared to the negative control group

Viral Infection Inhibition Test

In the present invention, *Berberis vulgaris* was extracted with ethanol, and chemical composition analyses and activity evaluations were conducted, and then alkaloid compounds such as Aromoline, Obamegine, Berbamine and Bersavine in the ethanol extract were identified and separated, all of which had the ability to inhibit viral infections.

Figure 2:
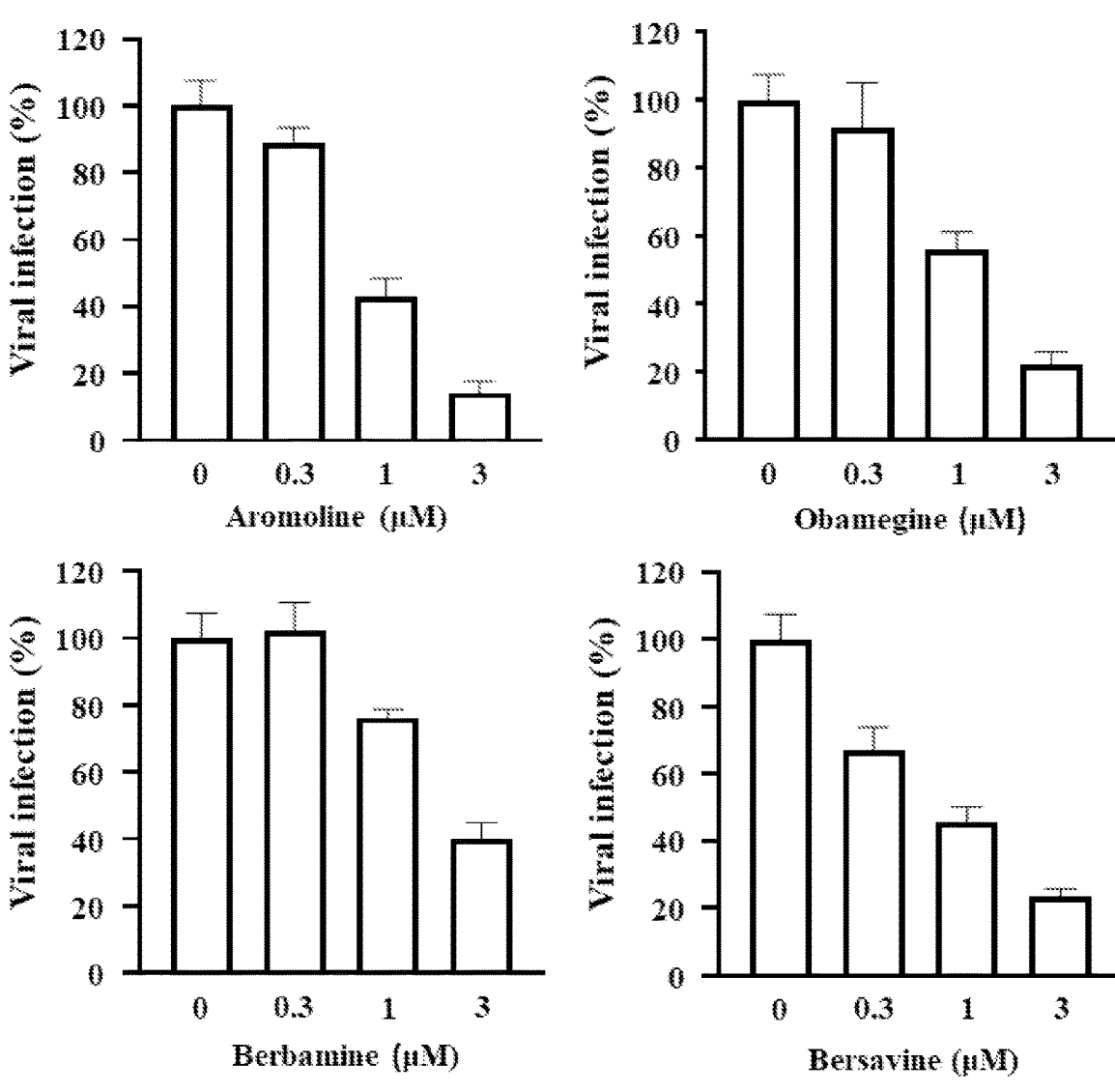
FIG. 2 shows the effect of each alkaloid compound of the present invention on the infection efficacy of the Omicron variant S protein pseudotyped lentivirus.

Preparation of virus solution: virus solution was added to 10% of DMEM to make the viral concentration of 5×104 R.I.U./mL 1 mL of the virus solution was taken and 11 μL of DMSO or a DMSO solution of specified compounds (Aromoline, Obamgine, Berbamine and Bersavine) was added into the taken virus solution to allow the virus and drug to react at 37° C. for 1 hour. ACE2-293T cells were seeded in a 96-well plate at a cell density of 1×104 cells/well, cultured at 37° C. in DMEM containing 10% of FBS and 10 μg/mL of blasticidin. After 10 hours of incubation to allow the cells to attach, 100 μL of the drug-virus mixture solution was added to infect the cells. After 24 hours of incubation at 37° C., the activities of these compounds against the D614G S protein group, the Delta S protein group, and the Omicron S protein group were quantified by luciferase activity assayed in the 96-well plates according to the manufacturer's instructions, the luciferase activity in the cells were examined to show the extent of viral infection. The calculation method was based on the luciferase activity reading value of the control group as 100%, and the extent of viral infection was determined by deducting the luciferase activity reading value of the control group from the luciferase activity reading value of each virus variant S protein group. Taking the Omicron variant strain S protein pseudotyped lentivirus as a representative, the infection inhibition trend of each compound against the Omicron variant strain S protein pseudotyped lentivirus could be seen in FIG. 2.

The half inhibition concentration (IC so) against the virus S protein was further calculated, and the results are shown in Table 2. The $IC_{50}$ of the E-64 compound (the compound regarded by current studies as a compound capable of inhibiting infection of SARS-CoV-2; the control group) for the D614G S protein group, the Delta S protein group and the Omicron S protein group were 23.12±0.63 μM, 23.06±1.30 μM and 22.69±1.28 μM, respectively.

TABLE 2

| Alkaloid compound | Half inhibition concentration of viral infection ($IC_{50}$) | | |
|---|---|---|---|
| | D614G | Delta | Omicron |
| Aromoline | 0.67 ± 0.09 | 0.47 ± 0.08 | 0.86 ± 0.12 |
| Obamegine | 1.40 ± 0.35 | 2.61 ± 0.42 | 1.19 ± 0.16 |
| Berbamine | 2.23 ± 0.49 | 2.56 ± 0.16 | 2.29 ± 0.29 |
| Bersavine | 1.24 ± 0.17 | 2.86 ± 0.13 | 1.71 ± 0.34 |
| Positive control (E-64) | 23.12 ± 0.63 | 23.06 ± 1.30 | 22.69 ± 1.28 |

Concentration required for half inhibition ($IC_{50}$, μM), data are represented as mean value ± standard deviation (n = 3).

Compared to the E-64 compound group, the half inhibition ($IC_{50}$) concentration of Aromoline for the D614G S protein group was 0.67±0.09 μM, and the half inhibition ($IC_{50}$) concentration for the Delta S protein group was 0.47±0.08 μM, the half inhibition ($IC_{50}$) concentration for the Omicron S protein group was ±0.12 μM. The half inhibition ($IC_{50}$) concentration of Obamegine for the D614G S protein group was 1.40±0.35 μM, for the Delta S protein group, the half inhibition ($IC_{50}$) concentration was 2.61±0.42 μM, for Omicron S protein group, the half inhibition ($IC_{50}$) concentration was 1.19±0.16 μM. The half inhibition ($IC_{50}$) concentration of Berbamine for the D614G S protein group was 2.23±0.49 μM, the half inhibition ($IC_{50}$) concentration for the Delta S protein group was 2.56±0.16 μM, the half inhibition ($IC_{50}$) concentration for the Omicron S protein group was 2.29±0.29 μM. The half inhibition ($IC_{50}$) concentration of Bersavine for the D614G S protein group was 1.24±0.17 μM, the half inhibition ($IC_{50}$) concentration for the Delta S protein group was 2.86±0.13 μM, and the half inhibition ($IC_{50}$) concentration for the Omicron S protein group was 1.71±0.34 μM.

The results indicated that Aromoline, Obamgine, Berbamine and Bersavine could effectively inhibit viral infections mediated by the spike proteins of various SARS-CoV-2 variants.

Alkaloid Cytotoxicity Analysis

The ACE2-293T cells were seeded in a 96-well plate, each well contained 1×10⁴ cells, and cultured at 37° C., 5% $CO_2$ for 10 hours. 10 mM of Aromoline, Obamegine, Berbamine and Bersavine DMSO solutions were prepared. 1 mL of 10% DMEM medium containing no phenol red indicator was taken, and 1 μL of DMSO or 10 mM of an alkaloid drug DMSO solution was added into the taken virus solution to prepare a one-thousandth diluted drug DMEM medium. After removing the ACE2-293T cell culture medium, 100 μL of DMEM medium containing a drug was added, after being cultured for 24 hours, 20 μL of WST-1 compound was added, reacted at 37° C. in the dark for 4 hours, then an enzyme-linked immunosorbent assay (ELISA) reader was used to read the absorbance at the wavelength of 450 nm, and the compared with the absorbance of control group which was set as 100%.

Figure 3:
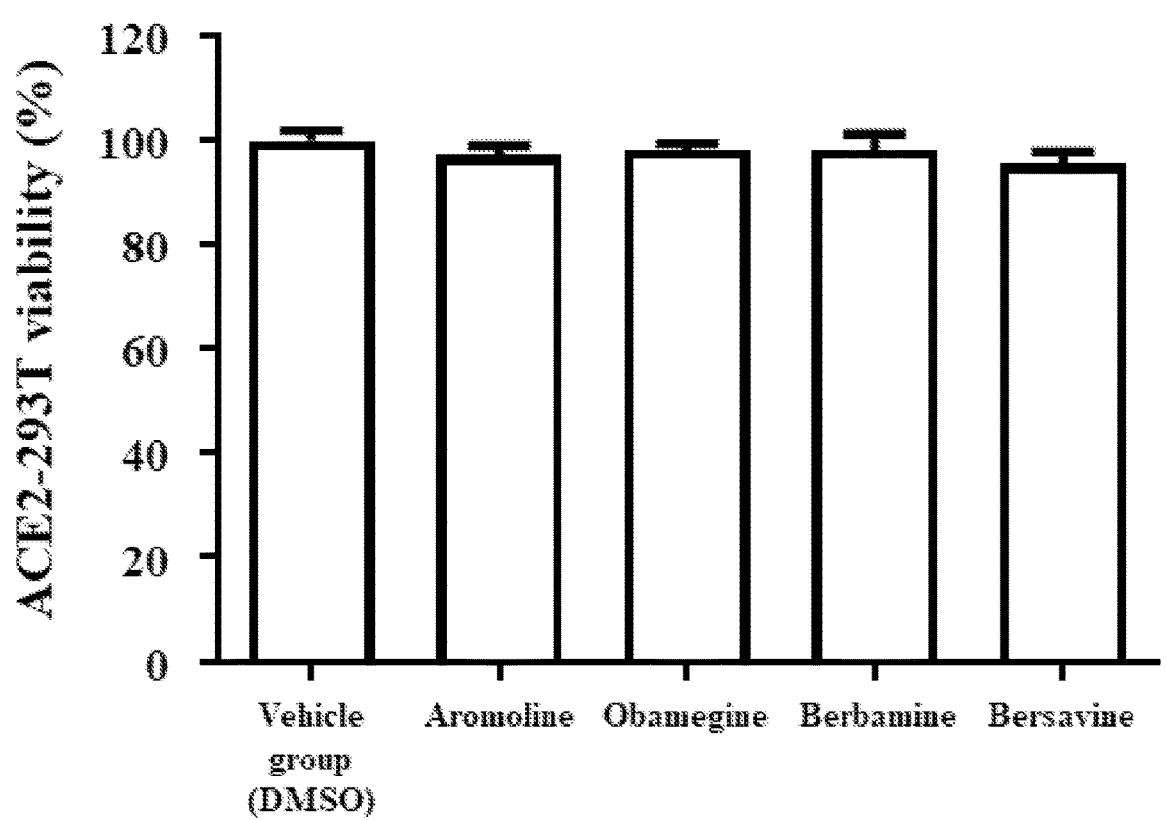
FIG. 3 shows the effect of each alkaloid compound in the present invention on the survival rate of ACE2-293T cells.

The cytotoxicity of the alkaloid compounds such as Aromoline, Obamegine, Berbamine and Bersavine to ACE2-293T cells was further investigated. In the present invention, a dose of 10 μM was used to conduct the cytotoxicity analysis, and the results showed that Aromoline, Obamegine, Berbamine or Bersavine caused no harms to the ACE2-293T cells (Table 3 and FIG. 3).

TABLE 3

| Group Name | Cell viability (%) |
|---|---|
| Vehicle group | 100.00 ± 1.12 |
| Aromoline | 97.10 ± 1.84 |
| Obamegine | 98.19 ± 1.11 |
| Berbamine | 98.15 ± 3.04 |
| Bersavine | 95.42 ± 2.33 |

Data are represented as mean value ± standard deviation (n = 3)
Compared to the vehicle group The present invention confirmed that the compounds such as Aromoline, Obamgine, Berbamine and Bersavine had effective effects on inhibiting viral infections mediated by spike proteins of different SARS-CoV-2 variant strains, and caused no toxicity to cells.

What is claimed is:

1. A method for inhibiting infection of SARS-CoV-2 in a subject, comprising administering a compound to the subject, wherein the compound is Obamegine or Bersavine, and the SARS-CoV-2 is omicron variant.

2. The method of claim 1, wherein the compound is extracted from a plant of the barberry family (Beriberidaceae).

3. The method of claim 2, wherein the plant of the barberry family (Beriberidaceae) is *Berberis vulgaris*.

4. The method of claim 1, wherein the compound is an alcohol extract extracted from the plant of the barberry family (Beriberidaceae).

5. The method of claim 4, wherein the plant of the barberry family (Beriberidaceae) is *Berberis vulgaris*.

6. The method of claim 1, wherein the compound inhibits infection of SARS-CoV-2 in the subject by blocking the binding of spike proteins on the SARS-CoV-2 and angiotensin-converting enzyme 2 on the subject's cells.

7. The method of claim 1, wherein the subject is a human or a mammal.

* * * * *